(12) United States Patent
Testi (10) Patent No.: US 9,944,906 B2
(45) Date of Patent: Apr. 17, 2018

(54) FRATAXIN MUTANTS

(71) Applicant: Fratagene Therapeutics, LLC, Dublin (IE)

(72) Inventor: Roberto Testi, Rome (IT)

(73) Assignee: FRATAGENE THERAPEUTICS S.R.L., Rome (IT)

( * ) Notice: Subject to any disclaimer, the term of this patent is extended or adjusted under 35 U.S.C. 154(b) by 85 days.

(21) Appl. No.: 14/940,043

(22) Filed: Nov. 12, 2015

(65) Prior Publication Data

US 2016/0060605 A1 Mar. 3, 2016

Related U.S. Application Data

(62) Division of application No. 13/812,516, filed as application No. PCT/IB2011/002511 on Jul. 27, 2011, now Pat. No. 9,217,019.

(60) Provisional application No. 61/368,576, filed on Jul. 28, 2010.

(51) Int. Cl.
*C12N 9/02* (2006.01)
*C07K 14/47* (2006.01)
*A61K 38/44* (2006.01)

(52) U.S. Cl.
CPC ............ *C12N 9/0091* (2013.01); *A61K 38/44* (2013.01); *C07K 14/47* (2013.01); *C12Y 116/03001* (2013.01)

(58) Field of Classification Search
None
See application file for complete search history.

(56) References Cited

U.S. PATENT DOCUMENTS

| 6,812,339 B1 * | 11/2004 | Venter | C12Q 1/6883 |
| | | | 435/6.11 |
| 8,703,749 B2 * | 4/2014 | Testi | A61K 31/63 |
| | | | 514/155 |

FOREIGN PATENT DOCUMENTS

WO 2006050819 5/2006

OTHER PUBLICATIONS

Condo et al In vivo maturation of human frataxin Human Molecular Genetics, 2007, vol. 16, No. 13 1534-1540 I.*
Condo et al Molecular control of the cytosolic aconitase/IRP1 switch by extramitochondrial frataxin Human Molecular Genetics, 2010, vol. 19, No. 7 1221-1229.*
Patent Cooperation Treaty, International Search Report and Written Opinion, International Patent Application No. PCT/IB2011/002511, dated Feb. 28, 2012, 12 pages.
Canadian Patent Application No. 2,806,303, Official Action, dated Jul. 10, 2015, 3 pages.
Canadian Patent Application No. 2,806,303, Official Action, dated Nov. 21, 2016, 3 pages.
EP15181464.7, "Extended European Search Report," dated Jan. 28, 2016, 7 pages.
EP15181464.7, "European Examination Report," dated Dec. 13, 2016, 6 pages.
Gottesfeld, "Small molecules affecting transcription in Friedreich ataxia," Pharmacology and Therapeutics, Elsevier,GB, vol. 116, No. 2, Sep. 26, 2007, pp. 236-248.
Marmolino et al., "Friedreich's Ataxia: from the (GAA)n repeat mediated silencing to new promising molecules for therapy," Cerebellum, vol. 8, No. 3, Sep. 2009, pp. 245-259.
Ngo et al., "Computational Complexity, Protein Structure Prediction, and the Levinthal Paradox," The Protein Folding Problem and tertiary Structure Prediction, K. Merc, Jr. and S. Le Grand Edition, 1994, pp. 491-495.
Rai, "HDAC Inhibitors 1-13 Correct Frataxin Deficiency in a Friedreich Ataxia Mouse Model," PLOS One, Public Library of Science, vol. 3, No. 4, Apr. 9, 2008, 8 pages.
Rufini et al., "Preventing the ubiquitin-proteasome-dependent degradation of frataxin, the protein defective in Friedreich's ataxia," Human Molecular Genetics, Oxford University Press, GB, vol. 20, No. 7, Apr. 1, 2011, pp. 1253-1261.
Wells, "Additivity of mutational effects in proteins," Biochemistry, vol. 29 (37), 1990, pp. 8509-8517.

* cited by examiner

*Primary Examiner* — Maria G Leavitt
(74) *Attorney, Agent, or Firm* — Kilpatrick Townsend & Stockton LLP (57) ABSTRACT

Described herein are compositions and methods for treating Friedreich's Ataxia (FRDA). In some aspects, mutant forms of frataxin which are resistant to ubiquitination are provided. In some aspects, pharmaceutical compositions comprising mutant frataxin are provided. In further aspects, methods of using mutant frataxin are provided.

7 Claims, 4 Drawing Sheets

```
         10         20         30         40         50         60
MWTLGRRAVA GLLASPSPAQ AQTLTRVPRP AELAPLCGRR GLRTDIDATC TPRRASSNQR 70         80         90        100        110        120
GLNQIWNVKK QSVYLMNLRK SGTLGHPGSL DETTYERLAE ETLDSLAEFF EDLADKPYTF 130        140        150        160        170        180
EDYDVSFGSG VLTVKLGGDL GTYVINKQTP NKQIWLSSPS SGPKRYDWTG KNWVYSHDGV 190        200        210
SLHELLAAEL TKALKTKLDL SSLAYSGKDA
```

SEQ ID NO: 1

Figure 1

```
atg tgg act ctc ggg cgc cgc gca gta gcc ggc ctc ctg gcg tca
ccc agc ccg gcc cag gcc cag acc ctc acc cgg gtc ccg cgg ccg
gca gag ttg gcc cca ctc tgc ggc cgc cgt ggc ctg cgc acc gac
atc gat gcg acc tgc acg ccc cgc cgc gca agt tcg aac caa cgt
ggc ctc aac cag att tgg aat gtc aaa aag cag agt gtc tat ttg
atg aat ttg agg aaa tct gga act ttg ggc cac cca ggc tct cta
gat gag acc acc tat gaa aga cta gca gag gaa acg ctg gac tct
tta gca gag ttt ttt gaa gac ctt gca gac aag cca tac acg ttt
gag gac tat gat gtc tcc ttt ggg agt ggt gtc tta act gtc aaa
ctg ggt gga gat cta gga acc tat gtg atc aac aag cag acg cca
aac aag caa atc tgg cta tct tct cca tcc agt gga cct aag cgt
tat gac tgg act ggg aaa aac tgg gtg tac tcc cac gac ggc gtg
tcc ctc cat gag ctg ctg gcc gca gag ctc act aaa gcc tta aaa
acc aaa ctg gac ttg tct tcg ttg gcc tat tcc gga aaa gat gct
```

SEQ ID NO: 2

SEQUENCE LISTING

```
<160> NUMBER OF SEQ ID NOS: 2

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45
```

```
Thr Cys Thr Pro Arg Arg Ala Ser Ser Asn Gln Arg Gly Leu Asn Gln
         50                  55                  60

Ile Trp Asn Val Lys Lys Gln Ser Val Tyr Leu Met Asn Leu Arg Lys
 65              70                  75                  80

Ser Gly Thr Leu Gly His Pro Gly Ser Leu Asp Glu Thr Thr Tyr Glu
                 85                  90                  95

Arg Leu Ala Glu Glu Thr Leu Asp Ser Leu Ala Glu Phe Phe Glu Asp
             100                 105                 110

Leu Ala Asp Lys Pro Tyr Thr Phe Glu Asp Tyr Asp Val Ser Phe Gly
             115                 120                 125

Ser Gly Val Leu Thr Val Lys Leu Gly Gly Asp Leu Gly Thr Tyr Val
         130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                 165                 170                 175

His Asp Gly Val Ser Leu His Glu Leu Leu Ala Ala Glu Leu Thr Lys
             180                 185                 190

Ala Leu Lys Thr Lys Leu Asp Leu Ser Ser Leu Ala Tyr Ser Gly Lys
         195                 200                 205

Asp Ala
    210

<210> SEQ ID NO 2
<211> LENGTH: 630
<212> TYPE: DNA
<213> ORGANISM: Homo sapiens

<400> SEQUENCE: 2
atgtggactc tcgggcgccg cgcagtagcc ggcctcctgg cgtcacccag cccggcccag    60
gcccagaccc tcacccgggt cccgcggccg gcagagttgg ccccactctg cggccgccgt   120
ggcctgcgca ccgacatcga tgcgacctgc acgccccgcc gcgcaagttc gaaccaacgt   180
ggcctcaacc agatttggaa tgtcaaaaag cagagtgtct atttgatgaa tttgaggaaa   240
tctggaactt tgggccaccc aggctctcta gatgagacca cctatgaaag actagcagag   300
gaaacgctgg actctttagc agagtttttt gaagaccttg cagacaagcc atacacgttt   360
gaggactatg atgtctcctt tgggagtggt gtcttaactg tcaaactggg tggagatcta   420
ggaacctatg tgatcaacaa gcagacgcca aacaagcaaa tctggctatc ttctccatcc   480
agtggaccta agcgttatga ctggactggg aaaaactggg tgtactccca cgacggcgtg   540
tccctccatg agctgctggc cgcagagctc actaaagcct taaaaaccaa actggacttg   600
tcttcgttgg cctattccgg aaaagatgct                                    630
```

FRATAXIN MUTANTS

RELATED APPLICATIONS

This application is a divisional of U.S. application Ser. No. 13/812,516, filed Jul. 27, 2011, now U.S. Pat. No. 9,217,019, which is the 35 USC § 371 national stage entry of International Application No. PCT/IB2011/002511, filed Jul. 27, 2011, and claims the benefit of the filing date of U.S. Application No. 61/368,576 filed on Jul. 28, 2010. These applications are incorporated by reference herein in their entireties.

FIELD

The present invention relates generally to compositions and methods useful for the treatment of Friedreich's Ataxia (FRDA). More specifically, the invention relates to the identification of a mutant frataxin protein and methods of delivering said protein into cells.

BACKGROUND

The disease. FRDA is an orphan disease that affects >20,000 individuals in Caucasian populations. Generally within 10 to 15 years from onset it leads to loss of deambulation and complete disability, with premature death often caused by cardiac insufficiency. Symptoms usually appear late in the first decade or early in the second decade of life, and include gait instability and general clumsiness. Gait ataxia has both cerebellar and sensory features, involves truncus and limbs, and is both progressive and generally unremitting. Swaying is common and, as it becomes more severe, eventually requires constant support and wheelchair use. Dysarthria occurs early in the disease and ultimately leads to complete speech impairment. Furthermore, dysphagia is a late feature and may require artificial feeding. Loss of peripheral neurons in dorsal root ganglia is the preeminent pathological finding. Ventricular hypertrophy characterizes the cardiac picture, and may progressively lead to congestive heart failure and fatal arrhythmias. A significant minority of patients also develop diabetes mellitus via mechanisms that are not yet clearly defined.

FRDA is caused by homozygous hyperexpansion of GAA triplets within the first intron of FXN, a highly conserved five-exon gene located on the long arm of human chromosome 9, coding for the protein frataxin. Pathological GAA expansions (from ~70 to >1,000 triplets) result in "sticky" DNA structures and epigenetic changes that severely reduce transcription of the FXN gene. FRDA patients live with 10-30% residual frataxin, and the severity of the disease is usually proportional to the number of GAA triplets and the consequent degree of frataxin reduction. A minority of FRDA patients, so-called compound heterozygotes, has pathological GAA expansions on one FXN allele and loss-of-function mutations on the other.

Current Therapeutic Approaches.

There is currently no specific therapy to prevent the progression of the disease. Most therapeutic approaches are aimed at reducing mitochondrial dysfunction and iron overload, and are therefore based on the use of anti-oxidants or iron chelators. Idebenone, a synthetic analog of ubiquinone with anti-oxidant properties, is currently under evaluation in phase III clinical trials. The iron chelator deferiprone and *Gingko-biloba* extract are other anti-oxidants presently in phase II clinical trials. Besides this, as levels of residual frataxin are crucial in determining the severity of the disease, many efforts have been put into the identification of molecules that increase frataxin transcription. A new class of histone de-acetylase (HDAC) inhibitors has been shown to reverse FXN silencing in FRDA cells and is now undergoing pre-clinical evaluation. The peroxisome proliferator-activated receptor gamma (PPAR-gamma) agonist Azelaoyl PAF has also recently been shown to increase FXN transcription, and a series of PPAR-gamma agonists are currently in pre-clinical phase. Another PPAR-gamma agonist, the widely used anti-diabetic pioglitazone, is entering a phase III trial for FRDA treatment. Finally, it was shown that erythropoietin appears to increase frataxin levels by an unknown mechanism. Recombinant erythropoietin as a treatment for FRDA is currently in phase II clinical trials.

While numerous approaches to treating FRDA have been explored, each of those approaches has significant limitations. Thus, a need exists in the art for new methods for more effectively treating FRDA.

SUMMARY

The present disclosure addresses long-felt needs in the field of medicine by providing novel compositions and methods for treating Friedreich's Ataxia.

Briefly stated, the present disclosure provides methods and compositions for the treatment of Friedreich's Ataxia (FRDA). The present disclosure relates to novel frataxin mutants, nucleotides encoding those frataxin mutants, methods of delivering the frataxin mutants, and methods of treating FRDA using the frataxin mutants.

Figure 1:
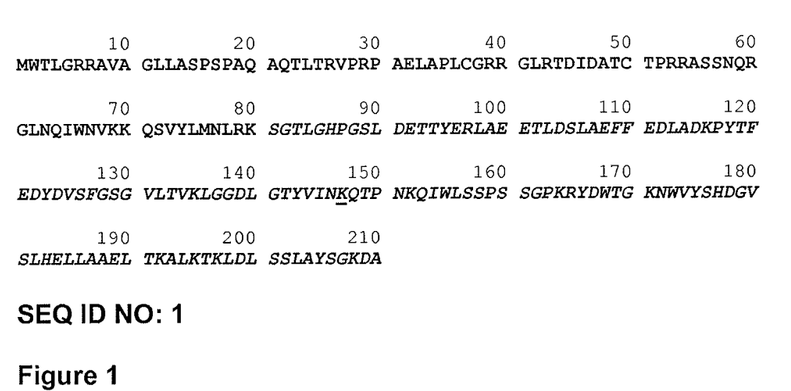
FIG. 1 shows the amino acid sequence of frataxin (SEQ ID NO:1). Amino acids 1-210 represent the frataxin precursor, and the italicized sequence (81-210) corresponds to the mature frataxin. The lysine at position 147 has been underlined.

In some aspects, the present disclosure provides isolated polypeptide having at least 75%, 80%, 85%, 90%, 95%, 98%, or 99% sequence identity to the amino acid sequence of FIG. 1 and comprising an R residue at a position corresponding to position 147 of FIG. 1.

In some aspects, the present disclosure provides for isolated nucleic acid molecule comprising a nucleic acid sequence which encodes a polypeptide having at least 75%, 80%, 85%, 90%, 95%, 98%, or 99% sequence identity to the amino acid sequence of FIG. 1.

Figure 2:
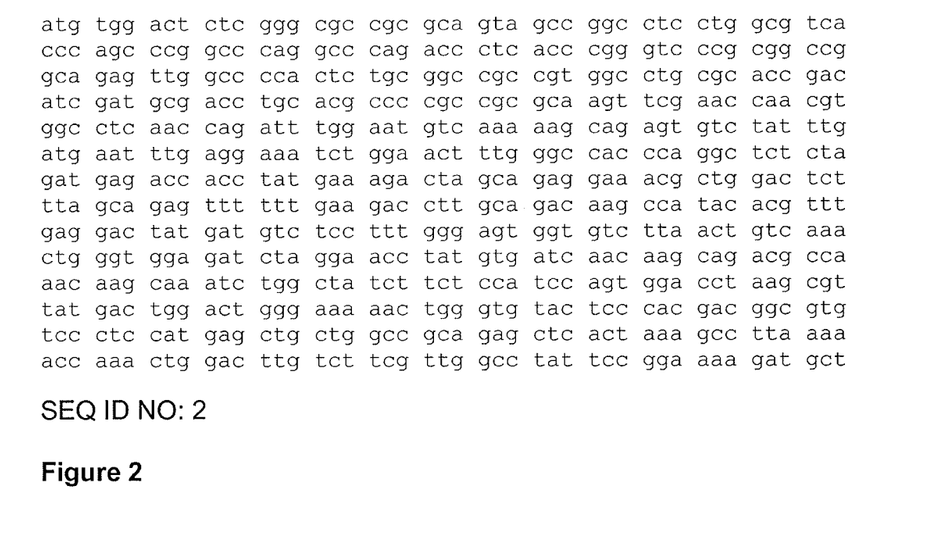
FIG. 2 shows the nucleotide sequence of the FXN gene, which encodes the human protein frataxin.

In some aspects, the present disclosure provides for isolated nucleic acid molecules, wherein the nucleic acid molecule comprises a nucleotide sequence having at least 75%, 80%, 85%, 90%, 95%, 98%, or 99% sequence identity to the full length sequence of FIG. 2.

In some aspects, the present disclosure provides for pharmaceutical compositions comprising a therapeutically effective amount of the isolated polypeptide of the present disclosure, optionally together with one or more pharmaceutically acceptable excipients, diluents, preservatives, solubilizers, emulsifiers, adjuvants, or carriers.

In further aspects, the present disclosure provides for methods of treating Friedreich's Ataxia, comprising administering to a subject the pharmaceutical compositions of the present disclosure.

In certain aspects, the present disclosure provides for methods of delivering the isolated polypeptide of any the present disclosure into a cell by a carrier selected from the group consisting of a liposome, a polymeric microcarrier, an exosome, a bacterial carrier, and a functional equivalent thereof. In further aspects, the isolated polypeptide has been fused in frame with a protein transduction domain. In still further aspects, the isolated polypeptide is delivered into the cell of a subject having Friedreich's Ataxia.

In some aspects, the present disclosure provides for methods of delivering the isolated polypeptide of the present disclosure into a cell by a carrier system selected from the

DETAILED DESCRIPTION

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and so forth. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Certain terms are discussed herein to provide additional guidance to the practitioner in describing the compositions, devices, methods and the like of aspects of the invention, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

All publications disclosed herein are incorporated by reference in their entirety for all purposes.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences.) As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art. See, e.g., Pearson, 1994, *Methods Mol. Biol.* 24:307-31 and 25:365-89 (herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W). Table 1 is a general BLOSUM62 amino acid substitution matrix.

et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOSUM62.

One skilled in the art may also use the ALIGN program incorporating the non-linear algorithm of Myers and Miller (*Comput. Appl. Biosci.* (1988) 4:11-17). For amino acid sequence comparison using the ALIGN program one skilled in the art may use a PAM120 weight residue table, a gap length penalty of 12, and a gap penalty of 4.

The length of polypeptide sequences compared for homology will generally be at least about 16 amino acid

TABLE 1

BLOSUM62 amino acid substitution matrix.
Reference: Henikoff, S. and Henikoff, J. G. (1992). Amino acid substitution matrices from protein blocks. Proc. Natl. Acad. Sci. USA 89: 10915-10919.

|   | A | B | C | D | E | F | G | H | I | K | L | M | N | P | Q | R | S | T | V | W | X | Y | Z |
|---|---|---|---|---|---|---|---|---|---|---|---|---|---|---|---|---|---|---|---|---|---|---|---|
| A | 4 | -2 | 0 | -2 | -1 | -2 | 0 | -2 | -1 | -1 | -1 | -1 | -2 | -1 | -1 | -1 | 1 | 0 | 0 | -3 | -1 | -2 | -1 |
| B | -2 | 6 | -3 | 6 | 2 | -3 | -1 | -1 | -3 | -1 | -4 | -3 | 1 | -1 | 0 | -2 | 0 | -1 | -3 | -4 | -1 | -3 | 2 |
| C | 0 | -3 | 9 | -3 | -4 | -2 | -3 | -3 | -1 | -3 | -1 | -1 | -3 | -3 | -3 | -3 | -1 | -1 | -1 | -2 | -1 | -2 | -4 |
| D | -2 | 6 | -3 | 6 | 2 | -3 | -1 | -1 | -3 | -1 | -4 | -3 | 1 | -1 | 0 | -2 | 0 | -1 | -3 | -4 | -1 | -3 | 2 |
| E | -1 | 2 | -4 | 2 | 5 | -3 | -2 | 0 | -3 | 1 | -3 | -2 | 0 | -1 | 2 | 0 | 0 | -1 | -2 | -3 | -1 | -2 | 5 |
| F | -2 | -3 | -2 | -3 | -3 | 6 | -3 | -1 | 0 | -3 | 0 | 0 | -3 | -4 | -3 | -3 | -2 | -2 | -1 | 1 | -1 | 3 | -3 |
| G | 0 | -1 | -3 | -1 | -2 | -3 | 6 | -2 | -4 | -2 | -4 | -3 | 0 | -2 | -2 | -2 | 0 | -2 | -3 | -2 | -1 | -3 | -2 |
| H | -2 | -1 | -3 | -1 | 0 | -1 | -2 | 8 | -3 | -1 | -3 | -2 | 1 | -2 | 0 | 0 | -1 | -2 | -3 | -2 | -1 | 2 | 0 |
| I | -1 | -3 | -1 | -3 | -3 | 0 | -4 | -3 | 4 | -3 | 2 | 1 | -3 | -3 | -3 | -3 | -2 | -1 | 3 | -3 | -1 | -1 | -3 |
| K | -1 | -1 | -3 | -1 | 1 | -3 | -2 | -1 | -3 | 5 | -2 | -1 | 0 | -1 | 1 | 2 | 0 | -1 | -2 | -3 | -1 | -2 | 1 |
| L | -1 | -4 | -1 | -4 | -3 | 0 | -4 | -3 | 2 | -2 | 4 | 2 | -3 | -3 | -2 | -2 | -2 | -1 | 1 | -2 | -1 | -1 | -3 |
| M | -1 | -3 | -1 | -3 | -2 | 0 | -3 | -2 | 1 | -1 | 2 | 5 | -2 | -2 | 0 | -1 | -1 | -1 | 1 | -1 | -1 | -1 | -2 |
| N | -2 | 1 | -3 | 1 | 0 | -3 | 0 | 1 | -3 | 0 | -3 | -2 | 6 | -2 | 0 | 0 | 1 | 0 | -3 | -4 | -1 | -2 | 0 |
| P | -1 | -1 | -3 | -1 | -1 | -4 | -2 | -2 | -3 | -1 | -3 | -2 | -2 | 7 | -1 | -2 | -1 | -1 | -2 | -4 | -1 | -3 | -1 |
| Q | -1 | 0 | -3 | 0 | 2 | -3 | -2 | 0 | -3 | 1 | -2 | 0 | 0 | -1 | 5 | 1 | 0 | -1 | -2 | -2 | -1 | -1 | 2 |
| R | -1 | -2 | -3 | -2 | 0 | -3 | -2 | 0 | -3 | 2 | -2 | -1 | 0 | -2 | 1 | 5 | -1 | -1 | -3 | -3 | -1 | -2 | 0 |
| S | 1 | 0 | -1 | 0 | 0 | -2 | 0 | -1 | -2 | 0 | -2 | -1 | 1 | -1 | 0 | -1 | 4 | 1 | -2 | -3 | -1 | -2 | 0 |
| T | 0 | -1 | -1 | -1 | -1 | -2 | -2 | -2 | -1 | -1 | -1 | -1 | 0 | -1 | -1 | -1 | 1 | 5 | 0 | -2 | -1 | -2 | -1 |
| V | 0 | -3 | -1 | -3 | -2 | -1 | -3 | -3 | 3 | -2 | 1 | 1 | -3 | -2 | -2 | -3 | -2 | 0 | 4 | -3 | -1 | -1 | -2 |
| W | -3 | -4 | -2 | -4 | -3 | 1 | -2 | -2 | -3 | -3 | -2 | -1 | -4 | -4 | -2 | -3 | -3 | -2 | -3 | 11 | -1 | 2 | -3 |
| X | -1 | -1 | -1 | -1 | -1 | -1 | -1 | -1 | -1 | -1 | -1 | -1 | -1 | -1 | -1 | -1 | -1 | -1 | -1 | -1 | -1 | -1 | -1 |
| Y | -2 | -3 | -2 | -3 | -2 | 3 | -3 | 2 | -1 | -2 | -1 | -1 | -2 | -3 | -1 | -2 | -2 | -2 | -1 | 2 | -1 | 7 | -2 |
| Z | -1 | 2 | -4 | 2 | 5 | -3 | -2 | 0 | -3 | 1 | -3 | -2 | 0 | -1 | 2 | 0 | 0 | -1 | -2 | -3 | -1 | -2 | 5 |

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild-type protein and a mutein thereof. See, e.g., GCG Version 6.1.

A preferred algorithm when comparing a particular polypeptide sequence to a database containing a large number of sequences from different organisms is the computer program BLAST (Altschul et al., *J. Mol. Biol.* 215:403-410 (1990); Gish and States, *Nature Genet.* 3:266-272 (1993); Madden residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

Nucleic Acid Molecule: The term "nucleic acid molecule" or "polynucleotide" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hair-pinned, circular, or in a padlocked conformation. If single stranded, the nucleic acid molecule can be the sense strand or the antisense strand. "Nucleic acid molecule" includes nucleic acid molecules which are not naturally occurring.

Isolated: An "isolated" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems. However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non native promoter sequence can be substituted (e.g. by homologous recombination) for the native promoter of a gene in the genome of a human cell, such that this gene has an altered expression pattern. This gene would now become "isolated" because it is separated from at least some of the sequences that naturally flank it. A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g. by human intervention. An "isolated nucleic acid" also includes a nucleic acid integrated into a host cell chromosome at a heterologous site, as well as a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized. The term also embraces nucleic acid molecules and proteins prepared by recombinant expression in a host cell as well as chemically synthesized nucleic acid molecules and proteins.

The term "percent sequence identity" or "identical" in the context of nucleic acid sequences refers to the nucleotides in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences. Pearson, *Methods Enzymol.* 183:63-98 (1990) (hereby incorporated by reference in its entirety). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference. Alternatively, sequences can be compared using the computer program, BLAST (Altschul et al., *J. Mol. Biol.* 215:403-410 (1990); Gish and States, *Nature Genet.* 3:266-272 (1993); Madden et al., *Meth. Enzymol.* 266:131-141 (1996); Altschul et al., *Nucleic Acids Res.* 25:3389-3402 (1997); Zhang and Madden, *Genome Res.* 7:649-656 (1997)), especially blastp or tblastn (Altschul et al., *Nucleic Acids Res.* 25:3389-3402 (1997)).

A particular, non-limiting example of a mathematical algorithm utilized for the comparison of sequences is that of Karlin and Altschul (*Proc. Natl. Acad. Sci.* (1990) USA 87:2264-68; *Proc. Natl. Acad. Sci. USA* (1993) 90: 5873-77) as used in the NBLAST and XBLAST programs (version 2.0) of Altschul et al. (*J. Mol. Biol.* (1990) 215:403-10). BLAST nucleotide searches can be performed with the NBLAST program, score=100, wordlength=12 to obtain nucleotide sequences homologous to nucleic acid molecules of the invention. To obtain gapped alignments for comparison purposes, Gapped BLAST can be utilized as described in Altschul et al. (*Nucleic Acids Research* (1997) 25(17): 3389-3402). When utilizing BLAST and Gapped BLAST programs, the default parameters of the respective programs (e.g., XBLAST and NBLAST) can be used (see website for BLAST hosted by the National Center for Biotechnology Information).

Purified: The term purified does not require absolute purity; rather, it is intended as a relative term. Thus, for example, a purified product preparation, is one in which the product is more concentrated than the product is in its environment within a cell. For example, a purified wax is one that is substantially separated from cellular components (nucleic acids, lipids, carbohydrates, and other peptides) that can accompany it. In another example, a purified wax preparation is one in which the wax is substantially free from contaminants, such as those that might be present following fermentation.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

"Specific binding" refers to the ability of two molecules to bind to each other in preference to binding to other molecules in the environment. Typically, "specific binding"

discriminates over adventitious binding in a reaction by at least two-fold, more typically by at least 10-fold, often at least 100-fold. Typically, the affinity or avidity of a specific binding reaction, as quantified by a dissociation constant, is about $10^{-7}$ M or stronger (e.g., about $10^{-8}$ M, $10^{-9}$ M or even stronger).

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., *Molecular Cloning: A Laboratory Manual*, 2d ed., Cold Spring Harbor Laboratory Press, Cold Spring Harbor, N.Y. (1989), page 9.51, hereby incorporated by reference. For purposes herein, "stringent conditions" are defined for solution phase hybridization as aqueous hybridization (i.e., free of formamide) in 6×SSC (where 20×SSC contains 3.0 M NaCl and 0.3 M sodium citrate), 1% SDS at 65° C. for 8-12 hours, followed by two washes in 0.2×SSC, 0.1% SDS at 65° C. for 20 minutes. It will be appreciated by the skilled worker that hybridization at 65° C. will occur at different rates depending on a number of factors including the length and percent identity of the sequences which are hybridizing.

A preferred, non-limiting example of stringent hybridization conditions includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 1×SSC plus 50% formamide at about 42-50° C.) followed by one or more washes in 0.3×SSC, at about 65-70° C. A preferred, non-limiting example of reduced stringency hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Intermediate ranges e.g., at 65-70° C. or at 42-50° C. are also within the scope of the invention. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$(° C.)=81.5+16.6($\log_{10}$[Na$^+$])+0.41 (% G+C)−(600/N), where N is the number of bases in the hybrid, and [Na$^+$] is the concentration of sodium ions in the hybridization buffer ([Na$^+$] for 1×SSC=0.165 M).

The skilled practitioner recognizes that reagents can be added to hybridization and/or wash buffers. For example, to decrease non-specific hybridization of nucleic acid molecules to, for example, nitrocellulose or nylon membranes, blocking agents, including but not limited to, BSA or salmon or herring sperm carrier DNA and/or detergents, including but not limited to, SDS, chelating agents EDTA, Ficoll, PVP and the like can be used. When using nylon membranes, in particular, an additional, non-limiting example of stringent hybridization conditions is hybridization in 0.25-0.5M $NaH_2PO_4$, 7% SDS at about 65° C., followed by one or more washes at 0.02M $NaH_2PO_4$, 1% SDS at 65° C. (Church and Gilbert (1984) *Proc. Natl. Acad. Sci. USA* 81:1991-1995,) or, alternatively, 0.2×SSC, 1% SDS.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 71%, 72%, 73%, 74%, 75%, 76%, 77%, 78%, 79%, 80%, 81%, 82%, 83%, 84%, 85%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

As used herein, a composition that is a "substantially pure" compound is substantially free of one or more other compounds, i.e., the composition contains greater than 80 vol. %, greater than 90 vol. %, greater than 95 vol. %, greater than 96 vol. %, greater than 97 vol. %, greater than 98 vol. %, greater than 99 vol. %, greater than 99.5 vol. %, greater than 99.6 vol. %, greater than 99.7 vol. %, greater than 99.8 vol. %, or greater than 99.9 vol. % of the compound; or less than 20 vol. %, less than 10 vol. %, less than 5 vol. %, less than 3 vol. %, less than 1 vol. %, less than 0.5 vol. %, less than 0.1 vol. %, or less than 0.01 vol. % of the one or more other compounds, based on the total volume of the composition.

Vector: The term "vector" as used herein refers to a nucleic acid molecule capable of transporting another nucleic acid to which it has been linked. One type of vector is a "plasmid," which refers to a circular double stranded DNA loop into which additional DNA segments may be ligated. Other vectors include cosmids, bacterial artificial chromosomes (BACs) and yeast artificial chromosomes (YACs). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors"). A vector can also include one or more selectable marker genes and other genetic elements known in the art. Suitable vectors for use in cyanobacteria include self-replicating plasmids (e.g., multiple copy and high-level expression) and chromosomal integration plasmids. Integration of vectors into the host genome or autonomously replicating vectors allow for gene expression in the host cell. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Frataxin Mutants

Because the severity of FRDA corresponds inversely to frataxin levels in the cell, most researchers have focused on the characterization of molecules that increase FXN transcription. Here, the present disclosure provides a novel method of maintaining adequate cellular frataxin levels, not by upregulating FXN transcription, but instead by developing a stable frataxin mutant precursor.

Human frataxin is synthesized as a 210 amino acid precursor (SEQ ID NO: 1) that is rapidly targeted to the mitochondria. Upon entrance into the mitochondria, the frataxin precursor undergoes proteolytic processing that generates mature frataxin, a 130 amino acid globular polypeptide that mostly resides within the mitochondrial matrix. Frataxin is involved in the proper functioning of the iron-sulfur cluster (ISC) machinery. Frataxin-defective cells in fact have reduced activity of ISC-containing enzymes, a general imbalance in intracellular iron distribution and increased sensitivity to oxidative stress. Frataxin is extremely conserved across species, from bacteria to humans, and is not redundant yet is absolutely required for life in higher eukaryotes.

It was observed that the frataxin precursor can be directly modified by ubiquitin and consequently targeted to the proteasome for degradation. Ubiquitin binds most commonly to lysine residues on substrates, and in the case of frataxin, it was determined that ubiquitination occurs at target residue K147 (FIG. 1). By site-specific mutagenesis of K147, a frataxin mutant that is less easily ubiquitinated is generated. In one embodiment, frataxin mutants have other than lysine at residue 147 (relative to SEQ ID NO:1).

In one embodiment, frataxin mutants have arginine at residue 147. Alternatively, frataxin mutants have histidine at residue 147. In another alternative, residue 147 is serine, threonine, asparagine or glutamine. In another alternative residue 147 is glycine, alanine, valine, isoleucine, leucine, methionine, phenylalanine, tyrosine or tryptophan. In another alternative, residue 147 is cysteine or proline. In another alternative, residue 147 is aspartic acid or glutamic acid.

By site-specific mutagenesis of the crucial lysine (K) into an arginine (R), frataxin K147R, a frataxin mutant that is not ubiquitinated was generated. Because frataxin K147R cannot be ubiquitinated, it is relatively resistant to proteasome-mediated degradation.

Frataxin mutants that have a residue other than lysine at position 147, including frataxin K147R, are introduced into frataxin-defective cells via one of several procedures. The protein can be delivered directly or after loading into liposomes, polymeric microcarriers, exosomes or bacterial carriers, either with or without having been fused to a protein transduction domain. Frataxin mutants can also be delivered to cells by packaging a viral, hybrid synthetic-viral, or non-viral system with mutant FXN cDNA and then administering to a subject. A subject having a frataxin deficiency can be effectively treated by receiving a therapeutically effective amount of a pharmaceutical composition of frataxin K147R, which optionally includes pharmaceutically acceptable excipients.

In some aspects, the present disclosure provides isolated polypeptide having at least 75%, 80%, 85%, 90%, 95%, 98%, or 99% sequence identity to SEQ ID NO: 1 and comprising a residue other than lysine at position corresponding to position 147 of SEQ ID NO: 1. In one aspect, the present disclosure provides isolated polypeptide having at least 75%, 80%, 85%, 90%, 95%, 98%, or 99% sequence identity to SEQ ID NO: 1 and comprising an R residue at a position corresponding to position 147 of SEQ ID NO: 1.

In some aspects, the present disclosure provides for isolated nucleic acid molecule comprising a nucleic acid sequence which encodes a polypeptide having at least 75%, 80%, 85%, 90%, 95%, 98%, or 99% sequence identity to SEQ ID NO: 1.

In some aspects, the present disclosure provides for isolated nucleic acid molecules, wherein the nucleic acid molecule comprises a nucleotide sequence having at least 75%, 80%, 85%, 90%, 95%, 98%, or 99% sequence identity to SEQ ID NO: 2.

A More Stable Frataxin as a Therapeutic Tool.

The FXN mutation of the single residue K147 into a residue other than lysine confers stability to the frataxin precursor and allows the generation of larger amounts of mature frataxin. In one embodiment, arginine replaces K 147. The increased stability of frataxin K147R compared to wild type frataxin can be a clear advantage for both gene-based and protein-based replacement therapeutic approaches to the treatment of Friedreich's Ataxia. Specifically, the frataxin K147R mutant is useful in the following areas of therapeutic intervention:

a) Protein Delivery.

Frataxin K147R can be delivered to frataxin-defective cells after loading into conventional liposomes, either as unilamellar vesicles (ULV) or multilamellar vesicles (MLV), as described in (Balasubramanian et al., 2010; Torchilin, 2005; Walde and Ichikawa, 2001) and references therein. To increase liposome stability, liposomes can be coated with polyethylene glycol (PEG) or encapsulated into polymeric matrices, such as chitosan (Werle and Takeuchi, 2009), alginate (Dai et al., 2006), or others. More stable encapsulated liposomes (capsosomes) can also be used, as described in (Stadler et al., 2009), or other liposomes (trigger liposomes) that release their content after an external trigger found in specific tissues or metabolic conditions can be used as well, as described in (Chen et al., 2004).

Alternatively, frataxin K147R can be delivered after entrapping into polymeric microcarriers, such as poly(lactic-co-glycolic) acid microparticles, as described in (Kim et al., 2009), long-lasting poly(e-caprolactone) (Coccoli et al., 2008), polyanhydrides such as poly(1,3-bis-(p-carboxyphenoxypropane)-co-sebacic anhydride) (P(CPP-SA)) microspheres (Sun et al., 2009), or core-shell microcapsules (Haidar et al., 2008). Frataxin K147R delivery can be achieved using more efficient systems such as polymeric nanoparticles (Singh and Lillard, 2009) (Hasadsri et al., 2009), polymeric micelles (Miller et al., 2009) or polymersomes (Onaca et al., 2009) (Christian et al., 2009), using polystyrene (Zauner et al., 2001), poly(lactic-co-glycolic) acid (Garnacho et al., 2008), PEG (Christian et al., 2009) (Dziubla et al., 2005) or other polymers.

Frataxin K147R can also be introduced into frataxin-defective cells by using bacteria such as *Listeria monocytogenes* as a delivery vehicle (Dietrich et al., 1998; Ikonomidis et al., 1997), or after entrapment into exosomes, which are naturally occurring nanovesicles released by cells (Simons and Raposo, 2009). Furthermore, frataxin K147R can be delivered by fusing it to antibodies or peptides, adding glycosylation sites, removing sites involved in activation, or PEGylating the protein by covalently attaching polyethylene glycol to the protein (Goodson and Katre, 1990). Finally, frataxin K147R can be directly administered via traditional methods of protein delivery such as microinjection and electroporation.

Delivery of frataxin K147R into frataxin-defective cells can be greatly enhanced by the use of protein transduction domains (PTD), including TAT, Antp, VP22 and others. The 11 peptide of the HIV-1 TAT protein is the most extensively investigated among PTDs (Rapoport and Lorberboum-Galski, 2009). TAT, or other PTDs, can therefore be used to modify liposomes, microcarriers, nanoparticles, micelles or exosomes containing frataxin K147R in order to facilitate entry into cells.

TAT or other PTDs can be directly fused in frame with frataxin K147R for a direct protein delivery approach to frataxin-defective cells, as described for other mitochondria-targeted proteins (Rector et al., 2008) (Rapoport et al., 2008).

In an example that closely resembles the intended delivery of frataxin into the mitochondria of FRDA cells, the mitochondrial protein lipoamide dehydrogenase (LAD), was in fact fused with TAT in a tentative therapeutic strategy to cure LAD deficiency (Rapoport et al., 2008). LAD deficiency (Maple syrup urine disease) is a rare autosomal recessive neurological disorder caused by mutations in the lipoamide dehydrogenase gene, and results in defective activity of LAD, a mitochondrial enzyme involved in amino acid and carbohydrate metabolism. Similarly to frataxin, the LAD precursor is imported into the mitochondria and subsequently proteolytically processed into a mature functional form.

Frataxin K147R can therefore be cloned downstream of TAT in a pTAT plasmid. The resulting construct can be used to transform *E. coli* competent cells, and then the TAT-frataxin K147R fusion protein recovered from the bacteria supernatant can be purified by protein liquid chromatography or by other methods (Rapoport et al., 2008). To test the activity of the purified product, the TAT-frataxin K147R fusion protein can be directly delivered to FRDA fibroblasts or lymphoblasts in culture, and subsequently the amount of intracellular and intramitochondrial frataxin can be quantitated by SDS-PAGE and western blot analysis. Assays commonly used to functionally test frataxin in cells, such as aconitase enzymatic activity, can be used to confirm the functional recovery of FRDA cells after the exposure to the TAT-frataxin K147R fusion protein. The efficacy of the TAT-frataxin K147R fusion protein can subsequently be tested in the available mouse model of FRDA, either by direct systemic infusion or by systemic infusion after encapsulation into any of the previously described micro or nanocarriers. Treated mice can then be scored biochemically (quantitation of frataxin levels in multiple tissues) and phenotypically (delay in disease progression, amelioration of sensomotory performance, etc.) for efficacy evaluation.

In all of the above mentioned examples of protein delivery, the possibility of loading the liposomes, microcarriers or exosomes with a more stable form of frataxin, i.e., the frataxin K147R mutant, or the possibility of fusing any PTD with a more stable form of frataxin, i.e., the frataxin K147R mutant, might result in a longer bioavailability of the administered frataxin, compared to similar approaches using wild-type frataxin, with possible reduction in the administration regimen, dosage, etc. that can reduce costs as well as discomfort and side effects for the patients.

In certain aspects, the present disclosure provides for methods of delivering the isolated polypeptide of any of the present disclosure into a cell by a carrier selected from the group consisting of a liposome, a polymeric microcarrier, an exosome, a bacterial carrier, and a functional equivalent thereof. In further aspects, the isolated polypeptide has been fused in frame with a protein transduction domain. In still further aspects, the isolated polypeptide is delivered into the cell of a subject having Friedreich's Ataxia.

In some aspects, the present disclosure provides for methods of delivering the isolated polypeptide of the present disclosure into a cell by a carrier system selected from the group consisting of a viral system, a hybrid synthetic-viral system, a non-viral system, and a functional equivalent thereof.

b) Gene Therapy.

Gene therapy for neurodegenerative diseases is attempted using viral or non-viral systems, as summarized in (Nanou and Azzouz, 2009) and references cited therein. Viral systems include adenoviruses, adeno-associated viruses, retroviruses, lentiviruses, herpes viruses, vaccinia viruses, poxviruses and others (Cardone, 2007) (Lim et al., 2010). Non-viral systems can make use of naked DNA or liposomes as carriers. Hybrid synthetic-viral systems can also be used (Nanou and Azzouz, 2009), as well as bacterial systems such as *Escherichia coli* or *Shigella flexneri* (Sizemore et al., 1995; Courvalin et al., 1995). Gene therapy approaches for FRDA, using a cDNA coding for the frataxin K147R mutant, can therefore be attempted using any of these systems.

Lentivirus-derived vectors in particular have been shown to allow effective gene expression in Spinal Muscolar Atrophy (SMA), another inherited monogenic disease characterized by peripheral neuron loss. SMA is due to mutations or deletion of the survival motor neuron (SMN) gene leading to depletion of SMN, a nuclear and cytoplasmic protein required for motorneuron survival. In an animal model for SMA, an equine infectious anemia virus (EIAV)-based lentivector, pseudotyped with rabies-G virus, has been shown to be effective in retrograde axonal transport and has been used to transduce spinal cord neurons following viral injections into muscles (Azzouz et al., 2004).

The frataxin K147R cDNA can therefore be cloned into a self-inactivating, rabies-G pseudotyped EIAV-based transfer vector (Azzouz et al., 2002). The EIAV-frataxin K147R lentivector can be first tested for its ability to express and reconstitute frataxin in frataxin-defective cells, by in vitro exposure to FRDA fibroblasts and subsequent quantitation by SDS-PAGE and western blot analysis. Assays commonly used to functionally test frataxin in cells, such as aconitase enzymatic activity, can be used to confirm the functional recovery of FRDA cells after lentivector exposure. The EIAV-frataxin K147R lentivector will then be injected at multiple sites into peripheral muscles of FRDA mice. Treated mice will then be scored biochemically (quantitation of frataxin levels in multiple tissues) and phenotypically (delay in disease progression, amelioration of sensomotory performance, etc.) for efficacy evaluation.

In all of the above mentioned examples of gene therapy, the possibility to package viral, non-viral or hybrid systems with a gene coding for a more stable form of frataxin, i.e., the frataxin K147R mutant, might result in a longer bioavailability of the expressed frataxin compared to similar approaches using wild type frataxin, with possible reduction in the administration regimen, dosage, etc. that can reduce costs as well as discomfort and side effects for the patients.

In some aspects, the present disclosure provides for pharmaceutical compositions comprising a therapeutically effective amount of the isolated polypeptide of the present disclosure, optionally together with one or more pharmaceutically acceptable excipients, diluents, preservatives, solubilizers, emulsifiers, adjuvants, or carriers.

Furthermore, a method of treating frataxin deficiency can include administering to a subject a therapeutically effective amount of a pharmaceutical composition of the frataxin K147R mutant. This pharmaceutical composition can further comprise one or more pharmaceutically acceptable excipients to provide a pharmaceutical composition. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants. A carbohydrate such as a sugar, a derivatized sugar such as an alditol, aldonic acid, an esterified sugar, and/or a sugar polymer can be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

A composition of the invention can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the mutant frataxin K147R or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (BASF, Mount Olive, N. J.); sorbitan esters; lipids, such as phospholipids such as lecithin and other phosphatidylcholines, phosphatidylethanolamines (although preferably not in liposomal form), fatty acids and fatty esters; steroids, such as cholesterol; chelating agents, such as EDTA; and zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the mutant frataxin K147R (e.g., when contained in a drug delivery system) in the composition will vary depending on a number of factors, but will optimally be a therapeutically effective dose when the composition is in a unit dosage form or container (e.g., a vial). A therapeutically effective dose can be determined experimentally by repeated administration of increasing amounts of the composition in order to determine which amount produces a clinically desired endpoint.

The amount of any individual excipient in the composition will vary depending on the nature and function of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

The compositions encompass all types of formulations and in particular those that are suited for injection, e.g., powders or lyophilates that can be reconstituted with a solvent prior to use, as well as ready for injection solutions or suspensions, dry insoluble compositions for combination with a vehicle prior to use, and emulsions and liquid concentrates for dilution prior to administration. Examples of suitable diluents for reconstituting solid compositions prior to injection include bacteriostatic water for injection, dextrose 5% in water, phosphate buffered saline, Ringer's solution, saline, sterile water, deionized water, and combinations thereof. With respect to liquid pharmaceutical compositions, solutions and suspensions are envisioned. Additional preferred compositions include those for oral, ocular, or localized delivery.

The pharmaceutical preparations herein can also be housed in a syringe, an implantation device, or the like, depending upon the intended mode of delivery and use. Preferably, the mutant frataxin K147R compositions described herein are in unit dosage form, meaning an amount of a conjugate or composition of the invention appropriate for a single dose, in a premeasured or prepackaged form.

Having now generally described various aspects and embodiments of the invention, the same will be more readily understood through reference to the following examples which are provided by way of illustration, and are not intended to be limiting, unless specified.

EXEMPLARY ASPECTS

Example 1

DNA Constructs

The pcDNA3-frataxin-HA construct was generated by subcloning the 3' HA-tagged frataxin from pBS-frataxin-HA into the pcDNA3 vector. The lysine mutant constructs were generated using the Quick-Change site-directed mutagenesis kit (Stratagene) with specific primers using either pcDNA5- frataxin or pcDNA3-frataxin-HA, as template. All the constructs generated were verified by DNA sequencing.

Example 2

Immunoblotting

Antibodies.
The following antibodies were used for western blot analysis: mAb anti-frataxin (MAB-10876, Immunological Science), mAb anti-HA (clone HA-7, Sigma), mAb anti-tubulin (Sigma), secondary antibody HRP-conjugated goat anti-mouse (Pierce).

Immunoblotting.
Cell extracts were prepared in modified RIPA buffer (10 mM sodium phosphate pH7.2, 150 mM NaCl, 1% Na deoxycholate, 0.1% SDS, 1% Np40, 2 mM EDTA) or IP buffer (50 mM Tris-HCl, pH 7.5, 150 mM NaCl, 1% Nonidet P-40, 5 mM EDTA, 5 mM EGTA) supplemented with Complete protease inhibitor cocktail and 2 mM N-Ethylmaleimide (NEM). For immunoblotting, 100 µg of protein extract were separated on 12% SDS-PAGE, blotted onto nitrocellulose membrane and detected with specific antibodies. All immunoblots were revealed by ECL (GE Healthcare). Densitometric analysis was performed using ImageJ software.

Example 3

Frataxin K147R Resistance to Proteasome-Mediated Degradation

Figure 3A:
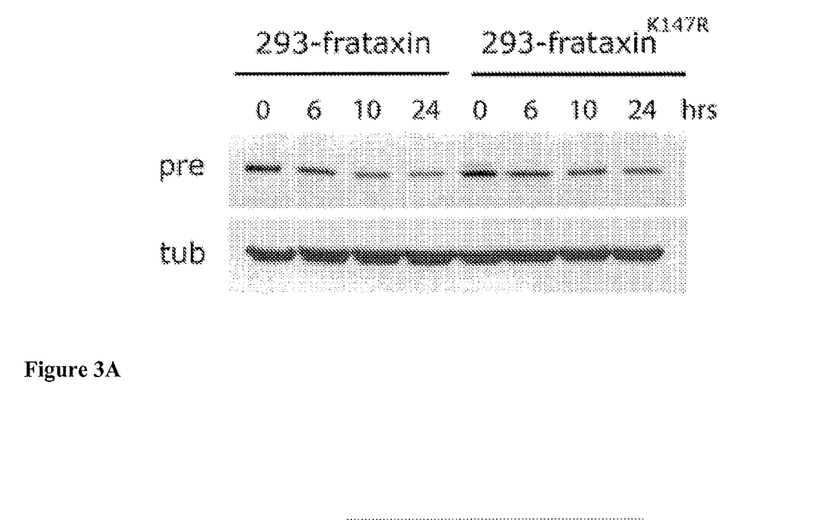
FIG. 3A shows 293 Flp-In cells stably expressing frataxin$^{1-210}$ (293-frataxin) or the K147R frataxin mutant (293-frataxin K147R). Cells were treated for the indicated times with 100 μg/ml cycloheximide (CHX) to block new protein synthesis. Proteins were resolved on SDS-PAGE and revealed with anti-frataxin antibody or anti-tubulin as a loading control. Pre: frataxin precursor. One representative experiment out of three performed with similar results is shown.
Figure 3B:
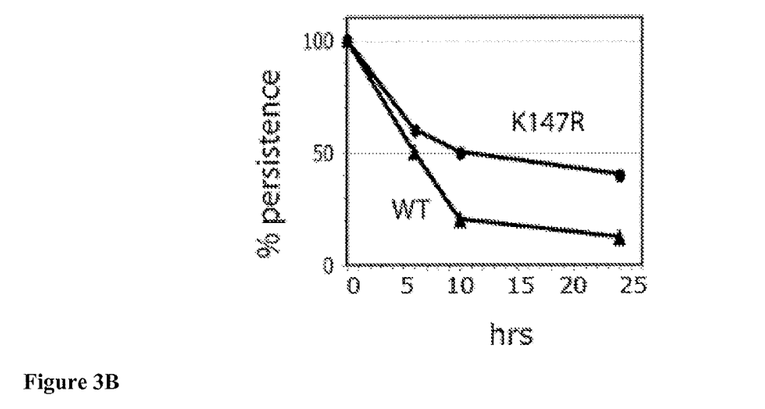
FIG. 3B shows densitometric analysis of frataxin precursor levels as shown in FIG. 3A normalized to tubulin levels. The graph shows the time-dependent decline upon CHX treatment. WT: 293-frataxin cells, K147R: 293-frataxin K147R cells.

The frataxin K147R mutant was stably expressed in Flp-In-293 cells to test whether the loss of the ubiquitin docking site granted the frataxin K147R mutant a relative resistance to proteasome-mediated degradation, thus increasing its stability. Flp-In-293 cells (Invitrogen) are human embryonic kidney HEK293 variants allowing the stable and isogenic integration and expression of a transfected gene. Flp-In-293 cells were maintained in DMEM supplemented with 10% FBS and transfected with the calcium/phosphate precipitation method. Briefly, cells were plated on 10 cm dishes and transfected with 10 µg total DNA. pcDNA5-frataxin K147R was used for the generation of 293 Flp-In stable cell line. Flp-In-293 cells stably expressing frataxin K147R were obtained from cultures in selection medium containing 100 µg/ml hygromycin B (Invitrogen). After exposure to cycloheximide to block new protein synthesis, the stability of the frataxin K147R precursor was monitored over time and compared to the stability of a wild type frataxin$^{1-210}$ precursor stably expressed in Flp-In-293 cells and similarly treated. FIG. 3A-B shows that the frataxin K147R precursor is significantly more stable (~45% of the input after 24 hrs) than the frataxin$^{1-210}$ precursor (~15% of the input after 24 hrs).

Example 4

Frataxin K147R Stability

Figure 4:
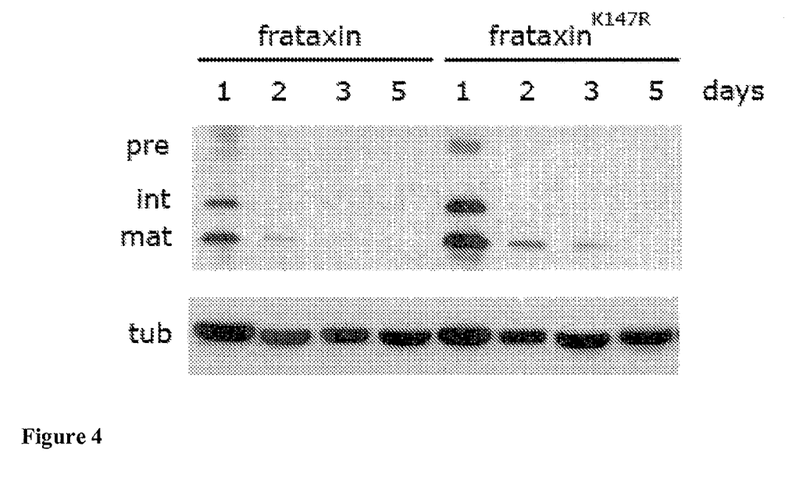
FIG. 4 shows HeLa cells that were transiently transfected with HA-tagged frataxin$^{1-210}$ or the HA-tagged K147R frataxin mutant. Protein extracts at the indicated days after transfection were resolved on SDS-PAGE and revealed with anti-HA antibody or anti-tubulin as a loading control. Pre: frataxin precursor; int: intermediate; mat: mature; tub: tubulin. One representative experiment out of three performed with similar results is shown.

In a different set of experiments, the HA-tagged frataxin K147R mutant or the HA-tagged wt frataxin$^{1-210}$ was transiently expressed in HeLa cells using pcDNA3-frataxin-HA K147R. Hela cells were maintained in DMEM supplemented with 10% FBS and transfected using Lipofectamine 2000 reagents (Invitrogen), according to manufacturer's instructions. This approach forces the ectopic expression of frataxin and allows the detection of all processing products, including the mature frataxin. The persistence of frataxin K147R was followed over a 5 day period upon transfection and compared to wild type frataxin. FIG. 4 shows that frataxin K147R is correctly processed and that its expression allows the accumulation of higher levels of frataxin precursor, intermediate and mature frataxin. Importantly, a significant amount of mature frataxin K147R can still be observed 3 days after transfection, a time point where wild type mature frataxin is no longer detectable.

The description of the aspects of the invention has been presented for the purpose of illustration; it is not intended to be exhaustive or to limit the invention to the precise forms disclosed. Persons skilled in the relevant art can appreciate that many modifications and variations are possible in light of the above teachings. It should be noted that the language used in the specification has been principally selected for readability and instructional purposes, and it may not have been selected to delineate or circumscribe the inventive subject matter. Accordingly, the disclosure of the aspects of the invention is intended to be illustrative, but not limiting, of the scope of the invention.

REFERENCES

Azzouz, M., Le, T., Ralph, G. S., Walmsley, L., Monani, U. R., Lee, D. C., Wilkes, F., Mitrophanous, K. A., Kingsman, S. M., Burghes, A. H., et al. (2004). Lentivector-mediated SMN replacement in a mouse model of spinal muscular atrophy. J Clin Invest 114, 1726-1731.

Azzouz, M., Martin-Rendon, E., Barber, R. D., Mitrophanous, K. A., Carter, E. E., Rohll, J. B., Kingsman, S. M., Kingsman, A. J., and Mazarakis, N. D. (2002). Multicistronic lentiviral vector-mediated striatal gene transfer of aromatic L-amino acid decarboxylase, tyrosine hydroxylase, and GTP cyclohydrolase I induces sustained transgene expression, dopamine production, and functional improvement in a rat model of Parkinson's disease. J Neurosci 22, 10302-10312.

Balasubramanian, V., Onaca, O., Enea, R., Hughes, D. W., and Palivan, C. G. (2010). Protein delivery: from conventional drug delivery carriers to polymeric nanoreactors. Expert Opin Drug Deliv 7, 63-78.

Cardone, M. (2007). Prospects for gene therapy in inherited neurodegenerative diseases. Curr Opin Neurol 20, 151-158.

Chen, T., McIntosh, D., He, Y., Kim, J., Tirrell, D. A., Scherrer, P., Fenske, D. B., Sandhu, A. P., and Cullis, P. R. (2004). Alkylated derivatives of poly(ethylacrylic acid) can be inserted into preformed liposomes and trigger pH-dependent intracellular delivery of liposomal contents. Mol Membr Biol 21, 385-393.

Christian, D. A., Cai, S., Bowen, D. M., Kim, Y., Pajerowski, J. D., and Discher, D. E. (2009). Polymersome carriers: from self-assembly to siRNA and protein therapeutics. Eur J Pharm Biopharm 71, 463-474.

Coccoli, V., Luciani, A., Orsi, S., Guarino, V., Causa, F., and Netti, P. A. (2008). Engineering of poly(epsilon-caprolactone) microcarriers to modulate protein encapsulation capability and release kinetic. J Mater Sci Mater Med 19, 1703-1711.

Courvalin, P., Goussard, S., and Grillot-Courvalin, C. (1995). Gene transfer from bacteria to mammalian cells. C R Acad Sci III 318, 1207-1212.

Dai, C., Wang, B., Zhao, H., Li, B., and Wang, J. (2006). Preparation and characterization of liposomes-in-alginate (LIA) for protein delivery system. Colloids Surf B Biointerfaces 47, 205-210.

Deitrich, G., Bubert, A., Gentschev, I., Sokolovic, Z., Simm, A., Catic, A., Kaufmann, S. H., Hess, J., Szalay, A. A., and Goebel, W. (1998). Delivery of antigen-encoding plasmid DNA into the cytosol of macrophages by attenuated suicide Listeria monocytogenes. Nat Biotechnol 16, 181-185.

Dziubla, T. D., Karim, A., and Muzykantov, V. R. (2005). Polymer nanocarriers protecting active enzyme cargo against proteolysis. J Control Release 102, 427-439.

Garnacho, C., Dhami, R., Simone, E., Dziubla, T., Leferovich, J., Schuchman, E. H., Muzykantov, V., and Muro, S. (2008). Delivery of acid sphingomyelinase in normal and niemann-pick disease mice using intercellular adhesion molecule-1-targeted polymer nanocarriers. J Pharmacol Exp Ther 325, 400-408.

Goodson, R. J., and Katre, N. V. (1990). Site-directed pegylation of recombinant interleukin-2 at its glycosylation site. Biotechnology 8, 343-346.

Haidar, Z. S., Hamdy, R. C., and Tabrizian, M. (2008). Protein release kinetics for core-shell hybrid nanoparticles based on the layer-by-layer assembly of alginate and chitosan on liposomes. Biomaterials 29, 1207-1215.

Hasadsri, L., Kreuter, J., Hattori, H., Iwasaki, T., and George, J. M. (2009). Functional protein delivery into neurons using polymeric nanoparticles. J Biol Chem 284, 6972-6981.

Ikonomidis, G., Portnoy, D. A., Gerhard, W., and Paterson, Y. (1997). Influenza-specific immunity induced by recombinant Listeria monocytogenes vaccines. Vaccine 15, 433-440.

Kim, B. S., Oh, J. M., Hyun, H., Kim, K. S., Lee, S. H., Kim, Y. H., Park, K., Lee, H. B., and Kim, M. S. (2009). Insulin-loaded microcapsules for in vivo delivery. Mol Pharm 6, 353-365.

Lim, S. T., Airavaara, M., and Harvey, B. K. (2010). Viral vectors for neurotrophic factor delivery: a gene therapy approach for neurodegenerative diseases of the CNS. Pharmacol Res 61, 14-26.

Miller, A. C., Bershteyn, A., Tan, W., Hammond, P. T., Cohen, R. E., and Irvine, D. J. (2009). Block copolymer micelles as nanocontainers for controlled release of proteins from biocompatible oil phases. Biomacromolecules 10, 732-741.

Nanou, A., and Azzouz, M. (2009). Gene therapy for neurodegenerative diseases based on lentiviral vectors. Prog Brain Res 175, 187-200.

Onaca, O., Enea, R., Hughes, D. W., and Meier, W. (2009). Stimuli-responsive polymersomes as nanocarriers for drug and gene delivery. Macromol Biosci 9, 129-139.

Rapoport, M., and Lorberboum-Galski, H. (2009). TAT-based drug delivery system—new directions in protein delivery for new hopes? Expert Opin Drug Deliv 6, 453-463.

Rapoport, M., Saada, A., Elpeleg, O., and Lorberboum-Galski, H. (2008). TAT-mediated delivery of LAD restores pyruvate dehydrogenase complex activity in the mitochondria of patients with LAD deficiency. Mol Ther 16, 691-697.

Rector, R. S., Payne, R. M., and Ibdah, J. A. (2008). Mitochondrial trifunctional protein defects: clinical implications and therapeutic approaches. Adv Drug Deliv Rev 60, 1488-1496.

Simons, M., and Raposo, G. (2009). Exosomes—vesicular carriers for intercellular communication. Curr Opin Cell Biol 21, 575-581.

Singh, R., and Lillard, J. W., Jr. (2009). Nanoparticle-based targeted drug delivery. Exp Mol Pathol 86, 215-223.

Sizemore, D. R., Branstrom, A. A., and Sadoff, J. C. (1995). Attenuated Shigella as a DNA delivery vehicle for DNA-mediated immunization. Science 270, 299-302.

Stadler, B., Chandrawati, R., Price, A. D., Chong, S. F., Breheney, K., Postma, A., Connal, L. A., Zelikin, A. N., and Caruso, F. (2009). A microreactor with thousands of subcompartments: enzyme-loaded liposomes within polymer capsules. Angew Chem Int Ed Engl 48, 4359-4362.

Sun, L., Zhou, S., Wang, W., Su, Q., Li, X., and Weng, J. (2009). Preparation and characterization of protein-loaded polyanhydride microspheres. J Mater Sci Mater Med 20, 2035-2042.

Torchilin, V. P. (2005). Recent advances with liposomes as pharmaceutical carriers. Nature reviews 4, 145-160.

Walde, P., and Ichikawa, S. (2001). Enzymes inside lipid vesicles: preparation, reactivity and applications. Biomol Eng 18, 143-177.

Werle, M., and Takeuchi, H. (2009). Chitosan-aprotinin coated liposomes for oral peptide delivery: Development, characterisation and in vivo evaluation. Int J Pharm 370, 26-32.

Zauner, W., Farrow, N. A., and Haines, A. M. (2001). In vitro uptake of polystyrene microspheres: effect of particle size, cell line and cell density. J Control Release 71, 39-51.

What is claimed:

1. An isolated or recombinant polynucleotide comprising a nucleic acid sequence which encodes a polypeptide having at least 90% sequence identity to the full length amino acid sequence of SEQ ID NO:1 and comprising an arginine (R) residue at a position corresponding to position 147 of SEQ ID NO:1.

2. The polynucleotide of claim 1, wherein the polypeptide has at least 95% sequence identity to the amino acid sequence of SEQ ID NO:1.

3. The polynucleotide of claim 1, wherein the polypeptide has at least 99% sequence identity to the amino acid sequence of SEQ ID NO:1.

4. The polynucleotide of claim 1, wherein the nucleic acid molecule comprises a nucleotide sequence having at least 90% sequence identity to the full length nucleotide sequence of SEQ ID NO:2.

5. A vector comprising the polynucleotide of claim 1.

6. A host cell comprising the polynucleotide of claim 1.

7. A pharmaceutical composition comprising a therapeutically effective amount of the isolated polynucleotide of claim 4 and one or more pharmaceutically acceptable excipients, diluents, preservatives, solubilizers, emulsifiers, adjuvants, or carriers.

\* \* \* \* \*